United States Patent [19]

Hobbs et al.

[11] Patent Number: 5,098,902
[45] Date of Patent: Mar. 24, 1992

[54] METHOD OF TREATING NEURODEGENERATIVE DISEASES

[75] Inventors: Sheila H. Hobbs, Dexter; Katharyn Spiegel, Ann Arbor, both of Mich.

[73] Assignee: Warner-Lambert Company, Morris Plains, N.J.

[21] Appl. No.: 758,924

[22] Filed: Sep. 11, 1991

Related U.S. Application Data

[62] Division of Ser. No. 672,066, Mar. 18, 1991, Pat. No. 5,075,305.

[51] Int. Cl.$^5$ .................................. A61V 31/535
[52] U.S. Cl. .......................................... 514/231.5
[58] Field of Search ...................... 514/231.5

[56] References Cited

U.S. PATENT DOCUMENTS

| | | | |
|---|---|---|---|
| 3,475,429 | 10/1969 | Woitun | 260/247.1 |
| 3,763,156 | 10/1973 | Woitun | 260/247.1 |
| 3,888,851 | 6/1975 | Narr | 260/243 |

FOREIGN PATENT DOCUMENTS

| | | | |
|---|---|---|---|
| 818990 | 8/1973 | Belgium . | |
| 0257102 | 3/1988 | European Pat. Off. | 31/505 |
| 0305184 | 3/1989 | European Pat. Off. | 487/4 |

*Primary Examiner*—S. J. Friedman
*Attorney, Agent, or Firm*—Ruth H. Newtson

[57] ABSTRACT

A method of treating a neurodegenerative disease which comprises administering 5-bromo-4-(4-morpholinyl)-2-pyrimidinamine or 4-(4-morpholinyl)-2-(1-piperazinyl)thieno[3,2-d]pyrimidine or a pharmaceutically acceptable salt thereof.

9 Claims, No Drawings

METHOD OF TREATING NEURODEGENERATIVE DISEASES

This is a divisional application of U.S. Ser. No. 07/672,066 filed Mar. 18, 1991 now U.S. Pat. No. 5,075,305.

FIELD OF INVENTION

The present invention relates to the treatment of neurodegenerative diseases which comprises administering 5-bromo-4-(4-morpholinyl)-2-pyrimidinamine or 4-(4-morpholinyl)-2-(1-piperazinyl)thieno[3,2-d]-pyrimidine or a pharmaceutically acceptable salt thereof.

BACKGROUND

Nerve growth factor (NGF) was first described by Buker (Anat. Rec. 102:369-389, 1948) and Levi-Montalcini (J. Exp. Zool. 116:321-362, 1951) as an activity secreted by a mouse sarcoma tumor implanted in a chick embryo. Both sensory ganglion and sympathetic ganglion neurons grew neurites into the sarcoma, which also supported the growth of peripheral neurons in culture. The factor, purified to homogeneity from mouse submandibular glands in 1956 by Levi Montalcini and Cohen (Proc. Natl. Acad. Sci. U.S.A. 42:571, 1956) consists of a complex (referred to as 7S NGF, from its sedimentation coefficient) comprised of three different subunits. NGF's neurotrophic activity resides entirely within the $\beta$-subunit (hereafter referred to as NGF), a dimer consisting of two equivalent monomers of approximately 13,000 dalton molecular weight.

A role for NGF as a neurotrophic factor in the peripheral nervous system (PNS) was rapidly established through both in vitro and in vivo experiments (Levi-Montalcini and Angeletti, Physiol. Rev. 48:534-569, 1968; Johnson, et al, Science 210:916-918, 1980). These studies demonstrated that sympathetic neurons of the PNS have an absolute requirement for NGF for survival throughout life, while many sensory neurons require NGF during certain periods of development. NGF is synthesized in the periphery by the nonneuronal target tissues innervated by the NGF-dependent neurons. Upon binding of NGF to its receptor, the NGF-receptor complex is internalized by the neuron and retrogradely transported back to the neuron cell body. NGF's intracellular mechanism of action is not yet fully elucidated.

It was not until 1983 that NGF was detected in the central nervous system (CNS) (Ayer-LeLievre, et al, Medical Biology 61:296-304, 1983). This discovery was preceded by the demonstration that the cholinergic neurons of the basal forebrain are responsive to NGF (Schwab, et al, Brain Res 168:473-483, 1979). These neurons possess NGF receptors which are indistinguishable from NGF receptors in the periphery. As in the PNS, NGF is synthesized by the target regions of the sensitive neurons, the hippocampus and the neocortex. NGF secreted by these target regions binds to its receptor and is internalized and transported back to the cholinergic cell bodies of the basal forebrain. The sensitivity of these neurons is especially interesting since these neurons are consistently depleted in Alzheimer's Disease (AD). It is possible, therefore, that an agent which enhances nerve growth factor's activity may be useful in treatment of CNS degenerative diseases like AD as well as peripheral neuropathies or other PNS degenerative disorders.

The term fibroblast growth factor may now be used to refer to any one of a family of peptide growth factors, but commonly refers to the best characterized members of the family, basic fibroblast growth factor (bFGF) and acidic fibroblast growth factor (aFGF) (Klagsbrun, Prog. Growth Factor Res. 1:207-235). Both bFGF and aFGF are 154 amino acid peptides of approximately 18,000 molecular weight. In addition, higher molecular weight forms of bFGF, but not aFGF, are found in some tissues. bFGF is found in most tissues, while aFGF is located primarily in the brain. Neither bFGF nor aFGF contain signal peptide sequences, suggesting that these peptides are not secreted but are likely cell-associated and/or extracellular matrix proteins. Both peptides bind to heparin, a property that has been exploited for purification of FGFs. Both low and high affinity binding sites for the FGFs have been identified. The low affinity sites, found on cell surfaces and in extracellular matrix, are likely heparin-like molecules that serve to concentrate FGF (Moscatelli, J. Cell Physiol. 131:123-130, 1987). High affinity receptors have been identified in many cell and tissue types, including nervous tissue, and some studies suggest that both bFGF and aFGF and possibly other members of the FGF family bind to the same receptor (Neufeld and Gospodarowicz, J. Cell Physiol. 136:537-542, 1988; Basilico, et al, J. Cell Biochem. Suppl. 13b:78, 1989). Receptors for aFGF and bFGF have now been cloned from several species (Ruta, et al, Proc. Natl. Acad. Sci. U.S.A. 86:8722-8726, 1989; Lee, et al, Science 245:57-60, 1989; Reid, et al, Proc. Natl. Acad. Sci. U.S.A. 87:1596-1600, 1990). The receptor sequences contain putative tyrosine kinase domains and both aFGF and bFGF induce the phosphorylation of both high and low molecular weight proteins in intact cells (Friesel, et al, Mol. Cell Biol. 9;1857-1865, 1989; Coughlin, et al. J. Biol. Chem. 263:988-993, 1988), suggesting that this kinase activity represents the major signal transduction pathway for the FGFs.

Both bFGF and aFGF have been implicated in differentiation and development in many tissues. In addition, the angiogenic properties of both peptides suggest that they may play a role in wound healing. Of particular interest is an increasing body of data suggesting that the FGFs function to promote neuronal differentiation and survival. Both bFGF and aFGF have been shown to induce neurite outgrowth in PC12 cells (Togari, et al, J. Neurosci. 5:307-316, 1985) and neurons (Lipton, et al, Proc. Natl. Acad. Sci. U.S.A. 85:2388-2392, 1988). In addition, bFGF has been shown to imitate nerve growth factor's ability to rescue both the cholinergic neurons of the basal forebrain and retinal ganglion cells following surgical transection of their project (Anderson, et al, Nature 332:360-361, 1988; Sievers, et al, Neurosci Letters 76:157-172, 1987). Whether bFGF is acting directly on the neurons or indirectly via interactions with glia is as yet unknown. Regardless, these studies suggest that modulation of fibroblast growth factor activity may be beneficial in neurodegenerative diseases.

Both 5-bromo-4-(4-morpholinyl)-2-pyrimidinamine and 4-morpholino-2-piperazinothieno[3,2-d]pyrimidine and pharmaceutically acceptable salts thereof enhance the effects of nerve growth factor and 4-morpholino-2-piperazinothieno[3,2-d]pyrimidine and pharmaceutically acceptable salts thereof enhance the effects of fibroblast growth factor.

PRIOR ART DISCLOSURES

U.S. Pat. No. 3,763,156, issued Oct. 2, 1973, specifically teaches the synthesis of 4-(4-morpholinyl)-2-(1-piperazinyl)thieno[3,2-d]-pyrimidine and its dihydrochloride salt in Example 1 thereof and teaches the use of the compound as an inhibitor of thrombocyte aggregation in blood. This compound is generically disclosed in U.S. Pat. No. 3,475,429, issued Oct. 28, 11969 and U.S. Pat. No. 3,888,851, issued June 10, 1975. The utility described for the '429 compounds is inhibition of platelet aggregation, and the utility described for the '851 compounds is inhibition of thrombocyte aggregation and adhesiveness. There are numerous journal references which describe the platelet aggregation inhibition properties of this compound.

No reference was found to 5-bromo 4-(4-morpholinyl)-2-pyrimidinamine.

Compounds of the following general formula are disclosed as therapeutic agents for neurological diseases in the peripheral nervous system and the central nervous system in European application 257,102:

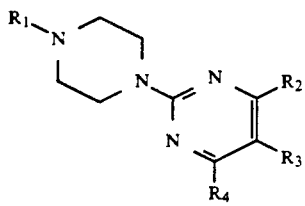

wherein $R_1$ can be hydrogen; $R_4$ is H, alkyl$C_{1-4}$, or alkylthio$C_{1-4}$; and $R_2$ and $R_3$ can form a 5- to 7-membered heterocyclic ring having a sulfur atom therein.

Compounds of the following general formula are disclosed in European application 305,184 as therapeutic agents for neurological diseases having the effect of regenerating and repairing nerve cells:

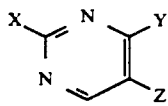

wherein X is an amino group including —NHalkyl$C_{1-4}$; Y is an amino group or a mono- or di-substituted alkyl$C_{1-4}$ amino group; and Z is methyl substituted by a $C_{2-5}$ alkoxycarbonyl or lower alkoxycarbonyl group; or Y and Z together form the group —N(R$_5$)—CO—CH$_2$—.

Belgian 818,990 (Derwent 17421W) describes as antithrombotic agents compounds of the following general formula

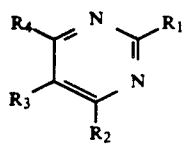

wherein $R_1$ can be alkoxy, morpholino, thiomorpholino, or piperazino; $R_2$ can be morpholino; $R_3$ can be bromo; and $R_4$ can be hydrogen.

SUMMARY OF THE INVENTION

This invention provides a method of enhancing the effects of nerve growth factor and a method of treating a neurodegenerative disease and, more particularly, a neurodegenerative disease selected from senile cognitive decline, Alzheimer's disease, myasthenia gravis, tardive dyskinesia, and dementia associated with Down's syndrome or Parkinson's disease by administering the compound 5-bromo-4-(4-morpholinyl)-2-pyridinamine or the compound 4-(4 morpholinyl)-2-(1-piperazinyl)thieno[3,2-d]-pyrimidine or a pharmaceutically acceptable salt of said compounds.

This invention also provides a method of enhancing the effect of fibroblast growth factor by administering 4-(4-morpholinyl) 2-(1-piperazinyl)thieno[3,2-d]pyrimidine or a pharmaceutically acceptable salt thereof.

This invention also provides as a novel compound 5-bromo-4-(4-morpholinyl)-2-pyrimidinamine and pharmaceutically acceptable salts thereof.

DETAILED DESCRIPTION OF INVENTION

The compound 5-bromo-4-(4-morpholinyl)-2-pyrimidinamine has the following structure:

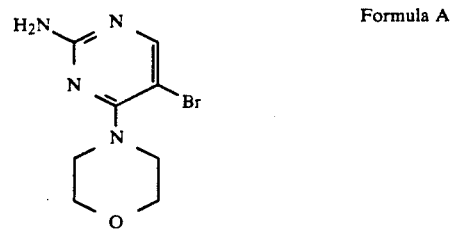

Formula A

The compound 4-(4-morpholinyl)-2-(1-piperazinyl)-thieno[3,2 d]pyrimidine has the following structure:

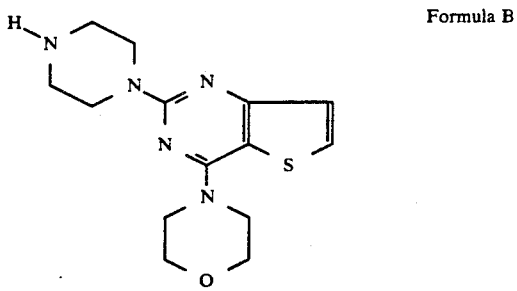

Formula B

The synthesis of the compound of Formula A is set forth herein as Example 1 The synthesis of the compound of Formula B is described in U.S. Pat. No. 3,763,156, issued Oct. 2, 1973, at column 9, lines 61 to 75 and column 10, lines 1 to 26, which portion is incorporated herein by reference.

Pharmaceutically acceptable acid addition salts of the compounds of Formulas A and B are illustratively hydrochloric, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methane and ethanesulfonic, hydroxymethane- and hydroxyethanesulfonic. (See, for example, "Pharmaceutical Salts," J. Pharm. Sci. 66(1):1–19 (1977).

The compounds of Formulas A and B have been found to enhance the activity of nerve growth factor.

The compound of Formula B has been found to enhance the activity of fibroblast growth nerve factor. These activities render the compounds of Formulas A and B useful in treating neurodegenerative diseases. In particular, these compounds are useful in treating senile cognitive decline and Alzheimer's disease. The compounds of Formulas A and B are also useful in treating myasthenia gravis, tardive dyskinesia, and dementia associated with Down's syndrome or Parkinson's disease. The utility of the compounds of Formulas A and B in treating these neurodegenerative diseases is demonstrated using culture of PC12 rat pheochromocytoma cells which have been shown to respond to nerve growth factor (NGF) (Tischler and Greene, Nature 258:341-342, 1975). The PC12 rat pheochromocytoma cells respond to NGF by differentiating into sympathetic neuron-like cells. The cells cease dividing, extend processes resembling neurites, and synthesize increased levels of neurotransmitters and neurotransmitter receptors. The testing protocol used in evaluating the compounds of Formulas A and B exploit the ability of NGF to increase the activity of the enzyme choline acetyltransferase (ChAT), a major synthetic enzyme for acetylcholine (Greene and Rein, Nature 268:349-351, 1977). The test procedure is the following.

PC12 cells were plated at a cell density of approximately $2.5 \times 10^5$ cells/well in rat tail collagen-coated 6-well cultivation plates having a well surface area of 9.62 cm$^2$. Cells were incubated for 7 days in 1.5 mL of a medium consisting of 85% RPMI 1640 supplemented with 10% horse serum and 5% fetal calf serum. The medium was replaced with fresh medium three times weekly. Test compounds were dissolved in H$_2$O or ethanol at a 100× concentration, and 15 μL of the 100× solution upon plating the cells and at each subsequent feeding. All test dishes were also treated with NGF or bFGF. In addition, each assay contained wells of PC12 cells treated with 10, 17.8, 32, 56, and 100 ng/mL of NGF.

Cells were harvested after 7 days in culture with the test compounds and NGF. The medium was aspirated and the cells rinsed with ice cold Puck's saline G, which was then also removed. The cells were then scraped, using a rubber policeman, in 40 μL of ice cold harvest buffer (20 mM Tris-HCl pH 8.6, 0.2% Triton X-100). Ten microliters of the resulting cell lysate were assayed for protein content by the method of Markewell, et al (Methods Enzymol. 72:296-303, 1981) and another 10 μL aliquot was assayed for ChAT activity using a modification of the method of Fonnum (Biochem. J. 115:465-472, 1969). Briefly, samples were incubated with an equal volume of reaction medium (100 mM NaH$_2$PO$_4$·0.6 M NaCl, 20 mM EDTA, 200 mM choline bromide, 20 mM NaCN, 20 μM physostigmine, 1 mg/mL albumin and 0.12 mg/mL $^{14}$C-acetyl coenzyme A, from New England Nuclear, 50 mCi/mmol) for 30 minutes at 37° C. The reaction was stopped by the addition of 3.5 mL of 10 mM Tris-HCl, pH 7.4, containing 200 μM acetylcholine bromide. Two milliliters of acetonitrile containing 5 mg/mL of tetraphenylboron were then added to each sample, followed by extraction with 10 mL of a 20:1 mixture of toluene and Liquifluor (a product of New England Nuclear). Samples were then counted in a liquid scintillation counter. Activity was expressed as pMol of product formed/mg protein/minute.

The test results are set forth below where the activity is expressed as a percent increase over the neuortrophic factor alone.

| Enhancement of NGF Effect with 4-(4-Morpholinyl)-2-(1-piperazinyl)thieno[3,2-d]pyrimidine | | | |
|---|---|---|---|
| Choline Acetyltransferase Activity (pMol/min/mg protein) | | | % Increase Over NGF |
| Without compound | | With 32 μM of Compound | With 32 μM of Compound |
| Control | 3.83 ± 2.0 | 10.34 ± 1.6 | 269.97 |
| NGF 10 ng/mL | 8.45 ± 1.3 | 17.45 ± 5.0 | 206.51 |
| NGF 17.8 ng/mL | 12.23 ± 3.3 | 25.17 ± 2.0 | 205.81 |
| NGF 32 ng/mL | 16.88 ± 4.6 | 34.08 ± 3.0 | 201.90 |
| NGF 56 ng/mL | 27.90 ± 6.2 | 44.02 ± 6.4 | 157.78 |
| NGF 100 ng/mL | 24.13 ± 4.0 | 42.10 ± 5.0 | 174.47 |

| Enhancement of bFGF Effect with 4-(4-Morpholinyl)-2-(1-piperazinyl)thieno[3,2-d]pyrimidine | | | |
|---|---|---|---|
| Choline Acetyltransferase Activity (pMol/min/mg protein) | | | % Increase Over bFGF |
| Without compound | | With 32 μM of Compound | With 32 μM of Compound |
| Control | 3.83 ± 2.0 | 10.34 ± 1.6 | 269.97 |
| bFGF 1 ng/mL | 7.35 ± 1.0 | 15.24 ± 3.3 | 207.35 |
| bFGF 3.2 ng/mL | 10.13 ± 1.50 | 23.23 ± 0.7 | 229.32 |
| bFGF 10 ng/mL | 10.45 ± 2.60 | 22.18 ± 3.4 | 212.25 |
| bFGF 32 ng/mL | 12.47 ± 1.10 | 24.11 ± 1.7 | 193.34 |
| bFGF 100 ng/mL | 12.53 ± 0.40 | 29.67 ± 10 | 236.79 |

| Enhancement of NGF Effect with 5-Bromo-4-(4-morpholinyl-2-pyrimidinamine | | |
|---|---|---|
| Choline Acetyltransferase Activity (pMol/min/mg protein) | | % Increase Over NGF |
| NGF 17.8 ng/mL | 30.18 ± 4.82 | |
| 1 μM + NGF 17.8 ng/mL | 36.51 ± 3.02 | 120.97 |
| 3.2 μM + NGF 17.8 ng/mL | 31.46 ± 9.13 | 104.24 |
| 10 μM + NGF 17.8 ng/mL | 52.33 ± 9.87 | 173.39 |
| 32 μm + NGF 17.8 ng/mL | 55.04 ± 11.29 | 182.37 |
| 100 μM + NGF 17.8 ng/mL | 83.13 ± 5.35 | 175.45 |

The compounds of Formulas A and B or a pharmaceutically acceptable salt thereof would be administered to a patient in need of treatment either orally or parenterally. The amount of compound to be administered would depend in part on the age, weight, and general condition of the patient. Typically, a patient would be closely monitored by a physician who could determine if the dosage amount or regimen of compound being administered was effective and well tolerated. The compounds of Formulas A and B or salts thereof would be administered admixed with a pharmaceutically acceptable carrier. An effective unit dose of the compounds would be from 0.083 to 1.67 mg/kg of body weight of the patient with a daily dose ranging from 1.66 to 3.34 mg/kg of body weight of the patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act is diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tablets preferably contain between about 5% to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral or parenteral administration, or suspensions, and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions for injection or infusion may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be capsule, cachet, or tablet itself, or it can be the appropriate number of any of these packaged forms.

EXAMPLE 1

5-Bromo-4-(4-morpholinyl)-2-pyrimidinamine

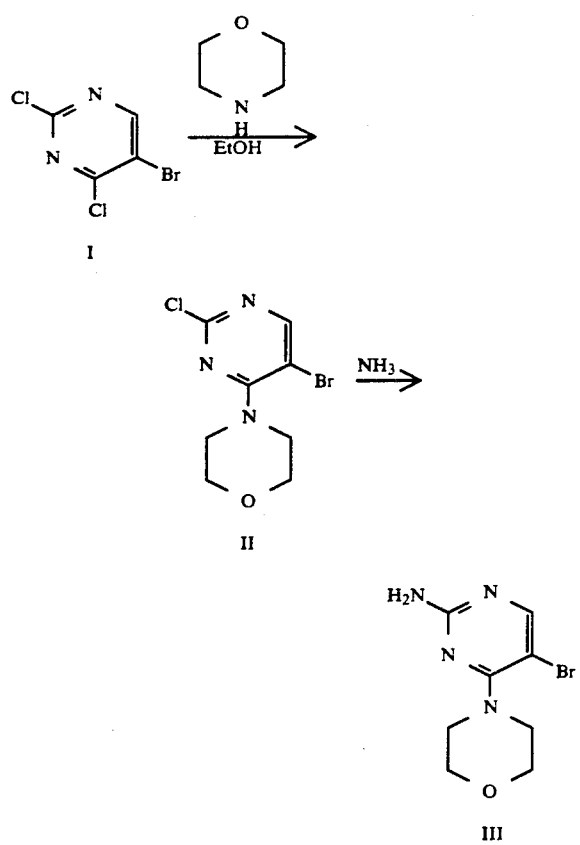

Compound I is prepared from 5-bromouracil by standard procedures (D. M. Mulvey, et al, J. Heterocyclic Chem. 10(1):79–83 (1973)).

2.5 g (0.0109 mol) of 5 bromo-2,4-dichloropyrimidine (I) is admixed with 100 mL of absolute ethanol. The resulting suspension is then vigorously stirred, and while stirring 2.1 g (0.0241 mole) of morpholine is added, accompanied by cooling to maintain the mixture at 20° C. The mixture is then stirred for 2 hours more at room temperature. The precipitate is thereafter separated by vacuum filtration and washed with water and ethanol, and dried in vacuo to yield 2.0 g (66%) of white solid. The product can be purified by recrystallization with absolute ethanol. 6.0 g (0.0215 mol) of 5-bromo-2-chloro-4-morpholinopyrimidine (II) is dissolved in 120 mL methanol. The solution is saturated with gaseous ammonia, sealed in a bomb, and heated at 45°–50° C. for 45 hours. The ammonium chloride salt is isolated by slurrying in methylene chloride and filtration. The filtrate is concentrated, triturated with ethyl acetate, filtered, and dried in vacuo to yield 2.64 g (47%) of an off-white solid.

We claim:

1. A method of treating a neurodegenerative disease in a patient in need thereof which comprises administering to said patient an effective amount of a compound selected from 5-bromo-4-(4-morpholinyl)-2-pyrimidinamine, 4-(4-morpholinyl)-2-(1-piperazinyl)thieno[3,2-d]pyrimidine or a pharmaceutically acceptable salt thereof.

2. The method of claim 1 wherein the neurodegenerative disease is selected from senile cognitive decline, Alzheimer's disease, myasthenia gravis, tardive dyskinesia, and dementia associated with Down's syndrome or Parkinson's disease.

3. The method of claim 2 wherein the compound is 5 bromo-4-(4-morpholinyl)-2-pyrimidinamine or a pharmaceutically acceptable salt thereof.

4. The method of claim 2 wherein the compound is 4-(4-morpholinyl)-2-(1-piperazinyl)thieno[3,2-d]-pyrimidine or a pharmaceutically acceptable salt thereof.

5. The method of claim 3 wherein the neurodegenerative disease is senile cognitive decline.

6. The method of claim 3 wherein the neurodegenerative disease is Alzheimer's disease.

7. The method of claim 4 wherein the neurodegenerative disease is senile cognitive decline.

8. The method of claim 4 wherein the neurodegenerative disease is Alzheimer's disease.

9. A method of enhancing the effect of fibroblast growth factor in a patient in need thereof which comprises administering to said patient an effective amount of 4-(4-morpholinyl)-2-(1-piperazinyl)thieno[3,2-d]pyrimidine or a pharmaceutically acceptable salt thereof.

* * * * *